(12) United States Patent
Steffan et al.

(10) Patent No.: US 6,395,567 B1
(45) Date of Patent: May 28, 2002

(54) PROCESS CONTROL USING IDEAL DIE DATA IN AN OPTICAL COMPARATOR SCANNING SYSTEM

(75) Inventors: Paul J. Steffan, Elk Grove; Allen S. Yu, Fremont, both of CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/109,114

(22) Filed: Jul. 2, 1998

(51) Int. Cl.[7] .......................... G01R 31/26; H01L 21/66
(52) U.S. Cl. ............... 438/16; 438/7; 438/14; 438/15; 438/460; 356/237
(58) Field of Search ............... 438/17, 15, 16, 438/460, 7; 356/237

(56) References Cited

U.S. PATENT DOCUMENTS 5,943,551 A  *  8/1999  Schemmel et al.
6,011,619 A  *  1/2000  Steffan et al.
6,017,771 A  *  1/2000  Yang et al.

OTHER PUBLICATIONS

Huang et al., Wafer Testing with Pairwise Comparisons, pp. 374–383, (IEEE), 1992.*
Kondo et al., A real time Process Control System for IC Testing, pp. 331–338, (IEEE), 1991.*
Huang et al., A Diagnosis Algorithm for Constant Degree Structures and Its Application to VLSI Circuit Testing, pp. 363–372, (IEEE), 1995.*

* cited by examiner

Primary Examiner—Long Pham
Assistant Examiner—Scott Brairton
(74) Attorney, Agent, or Firm—H. Donald Nelson

(57) ABSTRACT

A method of detecting defects on dice in semiconductor wafer wherein each dice in a layer is scanned and data from each dice is compared to data collected from an ideal dice obtained from the same level on a pre-production wafer. The data from each dice is compared in an optical comparator with data from the ideal dice stored in a register.

5 Claims, 5 Drawing Sheets

PROCESS CONTROL USING IDEAL DIE DATA IN AN OPTICAL COMPARATOR SCANNING SYSTEM

BACKGROUND OF THE INVENTION

1. Field of the Invention

This invention relates generally to a defect identification and classification methodology. More specifically, this invention relates to a defect identification and classification methodology that detects nonrandom defects. Even more specifically, this invention relates to a defect identification and classification methodology that detects uniformly induced defects.

2. Discussion of the Related Art

In order to remain competitive, a semiconductor manufacturer must continuously increase the performance of the semiconductor integrated circuits being manufactured and at the same time, reduce the cost of the semiconductor integrated circuits. Part of the increase in performance and the reduction in cost of the semiconductor integrated circuits is accomplished by shrinking the device dimensions and by increasing the number of circuits per unit area on a semiconductor integrated circuit chip. Another part of reducing the cost of a semiconductor integrated circuit chip is to increase the yield. As is known in the semiconductor manufacturing art, the yield of chips (also known as die or dice) from each wafer is not 100% because of defects during the manufacturing process. The number of good die obtained from a wafer determines the yield. As can be appreciated, die that must be discarded because of a defect or defects increases the cost of the remaining usable die because the cost of processing the wafer must be amortized over the usable die.

A single semiconductor die requires numerous process steps such as oxidation, etching, metallization and wet chemical cleaning. Some of these process steps involve placing the wafer on which the semiconductor die are being manufactured into different tools during the manufacturing process. The optimization of each of these process steps requires an understanding of a variety of chemical reactions and physical processes in order to produce high performance, high yield circuits. The ability to rapidly identify and classify the defects on a layer of a semiconductor chip is an invaluable aid to those involved in research and development, process, problem solving and failure analysis of integrated circuits.

One current method by which defects are rapidly detected and evaluated, is to employ a wafer scanning system which uses an optical site-to-site comparison technique to determine if a difference exists or if differences exist between adjacent dice. If a difference exists, the location of that difference is noted and is marked as a defect. To perform this task, the system scans a "swath" of a predetermined height across the surface of a wafer from one side to the opposite side and back. The scanning of swaths across the wafer is continued until the entire wafer is scanned or until a predetermined number of defects have been detected. This technique is valuable in determining if random defects occur, but is inadequate if the entire wafer is affected uniformly with induced defects, such as very wide or narrow CDs, over or under etch conditions (pitting, color variation) and unstripped resist.

Therefore, what is needed is a system in which optical data from an "ideal" die can be stored and used as a pre-scan condition that compares the optical data from the ideal die to optical data from die on production wafers.

SUMMARY OF THE INVENTION

According to the present invention, the foregoing and other objects and advantages are obtained by a method of detecting defects on a semiconductor wafer wherein scanned data from each dice on a processed layer on a semiconductor wafer is compared to data from an ideal dice obtained from the same layer on a pre-production wafer.

In another aspect of the invention, the scanned data is obtained by an optical scanning system.

The described method thus provides a method in which complete wafer level information can be obtained without impacting manufacturing throughput, allows for monitoring uniformly distributed process problems, enables monitoring process variations over time, allows monitoring process integrity on a macro as well as on a micro level and allows monitoring of process drift in individual equipment, evolution as will as abrupt change.

The present invention is better understood upon consideration of the detailed description below, in conjunction with the accompanying drawings. As will become readily apparent to those skilled in the art from the following description, there is shown and described an embodiment of this invention simply by way of illustration of the best mode to carry out the invention. As will be realized, the invention is capable of other embodiments and its several details are capable of modifications in various obvious aspects, all without departing from the scope of the invention. Accordingly, the drawings and detailed description will be regarded as illustrative in nature and not as restrictive.

BRIEF DESCRIPTION OF THE DRAWINGS

The novel features believed characteristic of the invention are set forth in the appended claims. The invention itself, however, as well as a preferred mode of use, and further objects and advantages thereof, will best be understood by reference to the following detailed description of an illustrative embodiments when read in conjunction with the accompanying drawings, wherein:

DETAILED DESCRIPTION

Reference is now made in detail to specific embodiments of the present invention which illustrate the best mode presently contemplated by the inventors for practicing the invention.

Figure 1:
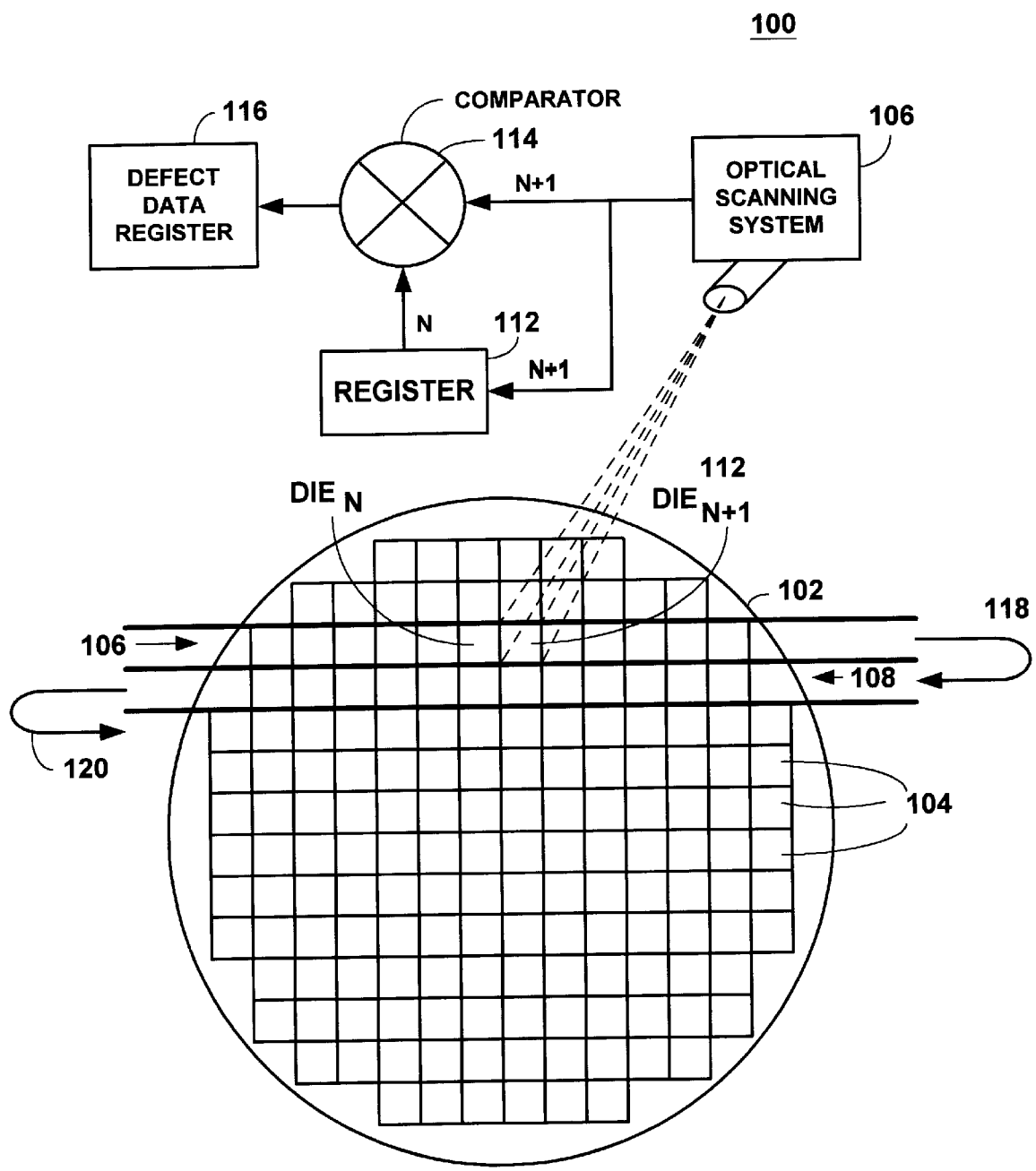
FIG. 1 is a schematic diagram of a prior art wafer scanning system and methodology.

FIG. 1 is a schematic diagram of a prior art wafer scanning system 100 and methodology. A production wafer 102 is shown with die such as the ones shown at 104. An optical scanning system 106 optically scans the die 104 on the wafer 102 in swaths such as the swaths 106 & 108. The optical scanning system 106 scans the die 104 one at a time such as die N at 110. Optical data from die N 110 is transferred to a register 112 where it is stored until the optical scanning system 106 optically scans the next die N+1 113. The optical data from die N+1 is transferred to comparator 114 where it is compared to the optical data from die N 110 that has been stored in register 112. The optical data from die N+1 113 is input to register 112 where it displaces data stored from the previous die. If there is a defect or defects, comparator 114 transfers the defect data to defect data register 116. The scanning of wafer 102 is continued as shown from swath 106 to swath 108 as indicated by arrows 118 & 120 until a predetermined number of defects has been received by defect data register 116 or until the entire wafer has been scanned.

Figure 2:
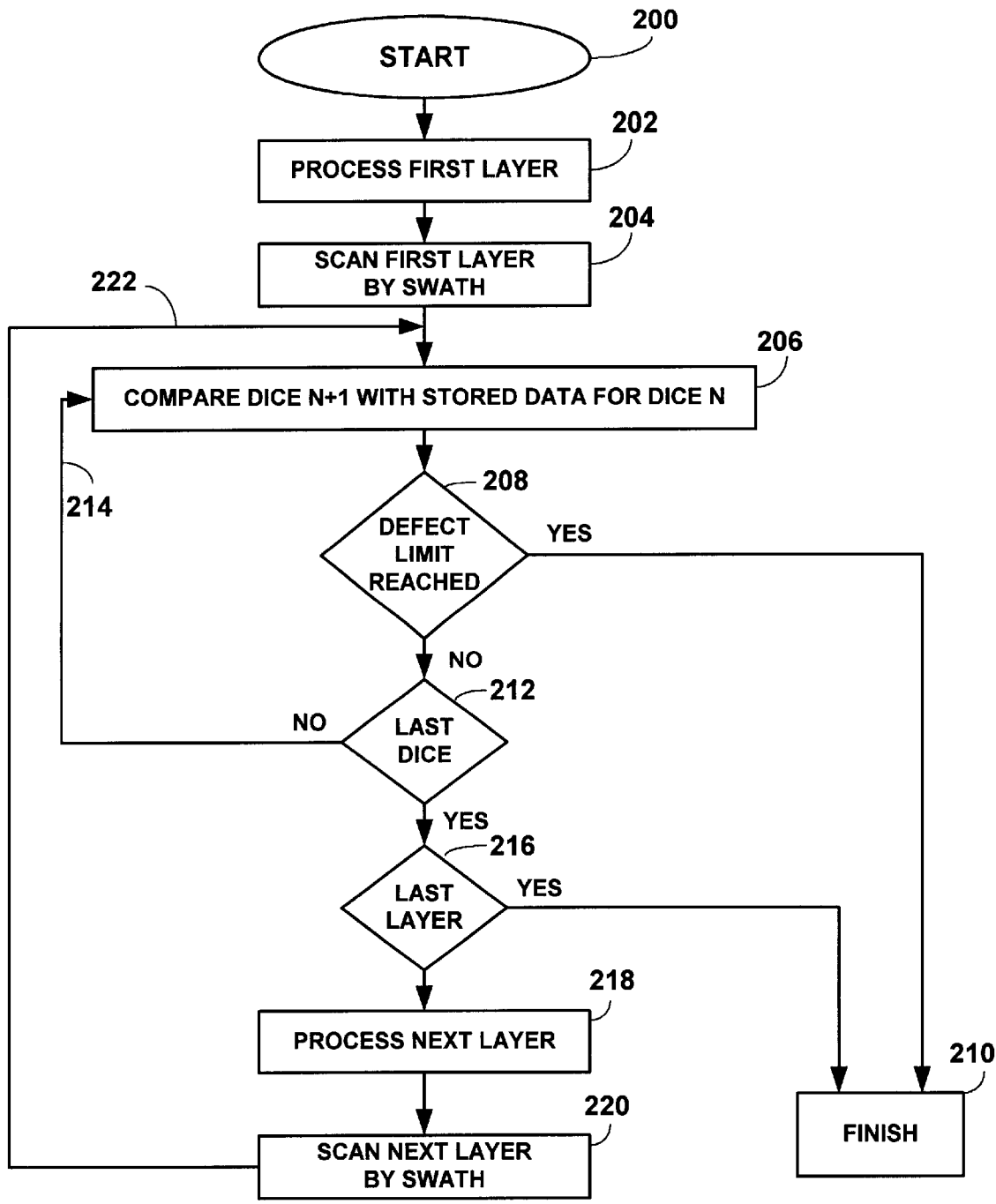
FIG. 2 is a flow diagram of the prior art methodology diagrammed in FIG. 1.

FIG. 2 is a flow diagram of the prior art methodology diagrammed in FIG. 1. The methodology starts at 200 by starting a wafer in a manufacturing process. A first layer is processed on the wafer as shown at 202. It is noted that there are multiple process layers on a typical semiconductor device; however, not all layers are scanned by the optical scanning system because some layers do not have significant processes that may result in significant defects. The first layer to be scanned is scanned by swath as indicated at 204. During the scanning process, the scanning process optically scans a die N and stores the optical data for die N in register 112 (FIG. 1). The scanning process optically scans the next die N+1, and compares the optical data from die N+1 to the stored optical data for die N as shown at 206. If defects are detected or if a defect is detected, it is determined at 208 if a predetermined defect limit has been reached. If the predetermined defect limit has been reached, the process is finished as shown at 210. If the predetermined defect limit has not been reached, it is determined at 212 if the dice just scanned is the last die. If not, the next die is scanned, as indicated at 214. If the last die has been scanned, it is determined at 216 if the layer just scanned is the last layer. If not, the next layer is processed as indicated at 218. The next layer is scanned, as indicated at 220 and the process of comparing adjacent dice is repeated as shown at 222.

Figure 3:
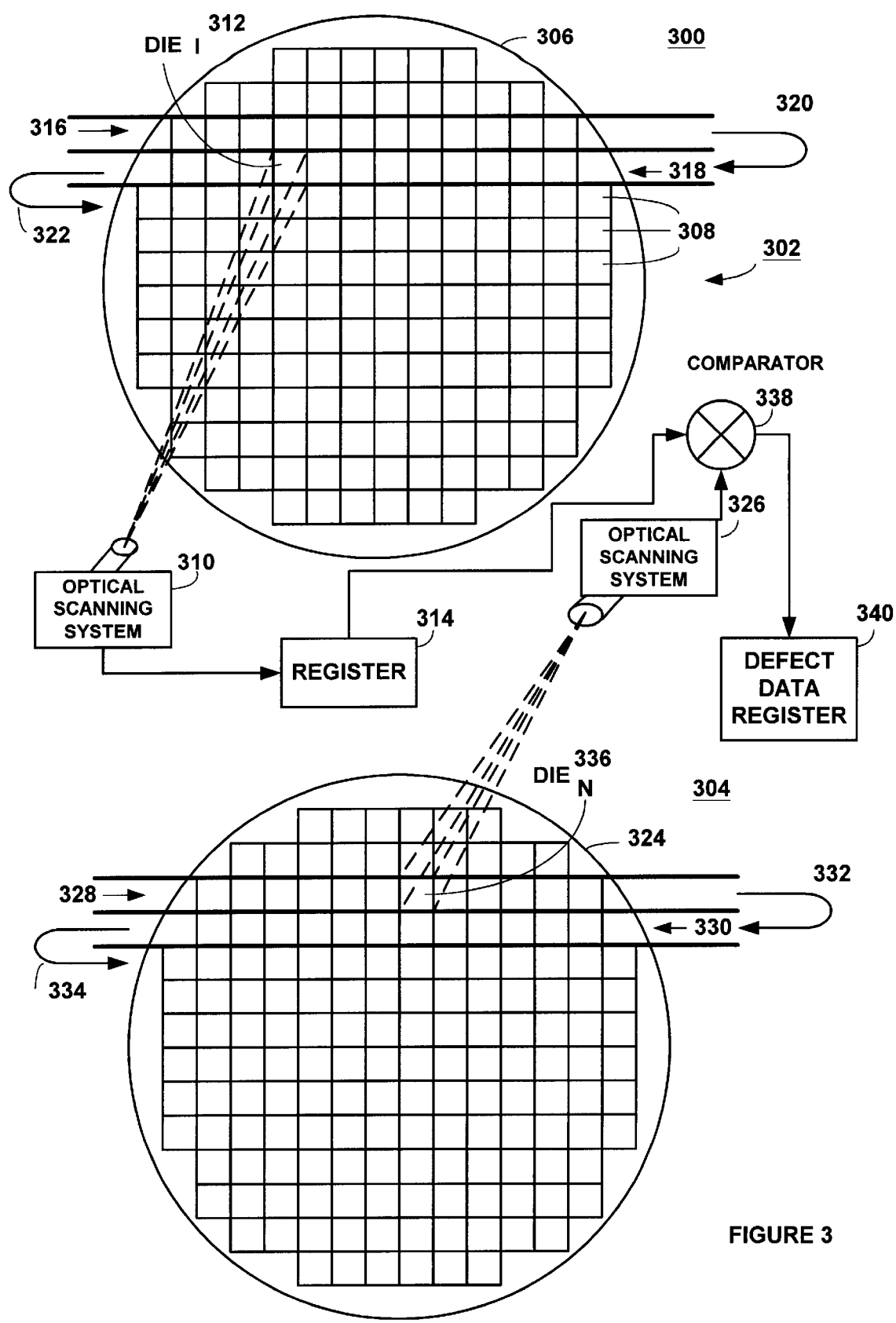
FIG. 3 is a schematic diagram of a wafer scanning system and methodology in accordance with the present invention.

Referring to FIG. 3 there is shown a diagrammatic schematic of a wafer scanning system 300 and methodology in accordance with the present invention. The methodology of the present invention includes obtaining "ideal" optical data for a die from an initial wafer as shown at 302 and comparing the ideal optical data to die on a production wafer as shown at 304. Initially, each layer of one or more pre-production wafers 306 with die 308 formed on the wafer 306 is scanned by an optical scanning system 310 and optical data for an "ideal" die I 312 for each layer is stored in a register 314. The optical scanning system 310 scans the wafer 306 by swath as indicated by swaths 316 and 318 and arrows 320 and 322. The ideal optical die data is stored as part of the recipe setup for a particular device and layer. This technique can be used to scan for catastrophic failure and therefore, smaller differences can be ignored. This means that the scan could be done at a higher magnification than is normally used for scanning for regular defects.

This method can also be used for analysis of a wafer manufacturing process and the optical scanning method can be used to scan at different magnifications and the wafer can be monitored on a macro as well as on a micro level. The comparison of optical scanning data from production wafers from later lots would allow for the accurate monitoring of parameter drift in the manufacturing process as well as an abrupt change in the manufacturing process.

A production wafer 324 is scanned by swath by an optical scanning system 326 by swath as indicated by swaths 328 and 330 and arrows 332 and 334. The scanned optical data from each die N 336 transferred by the optical scanning system 326 to comparator 338 where it is compared to the optical data for the ideal die I 312 that has been stored in register 314. Information concerning defects is transferred from comparator 338 to defect data register 340. This process is repeated until all the layers of a production wafer are processed and scanned.

Figure 4:
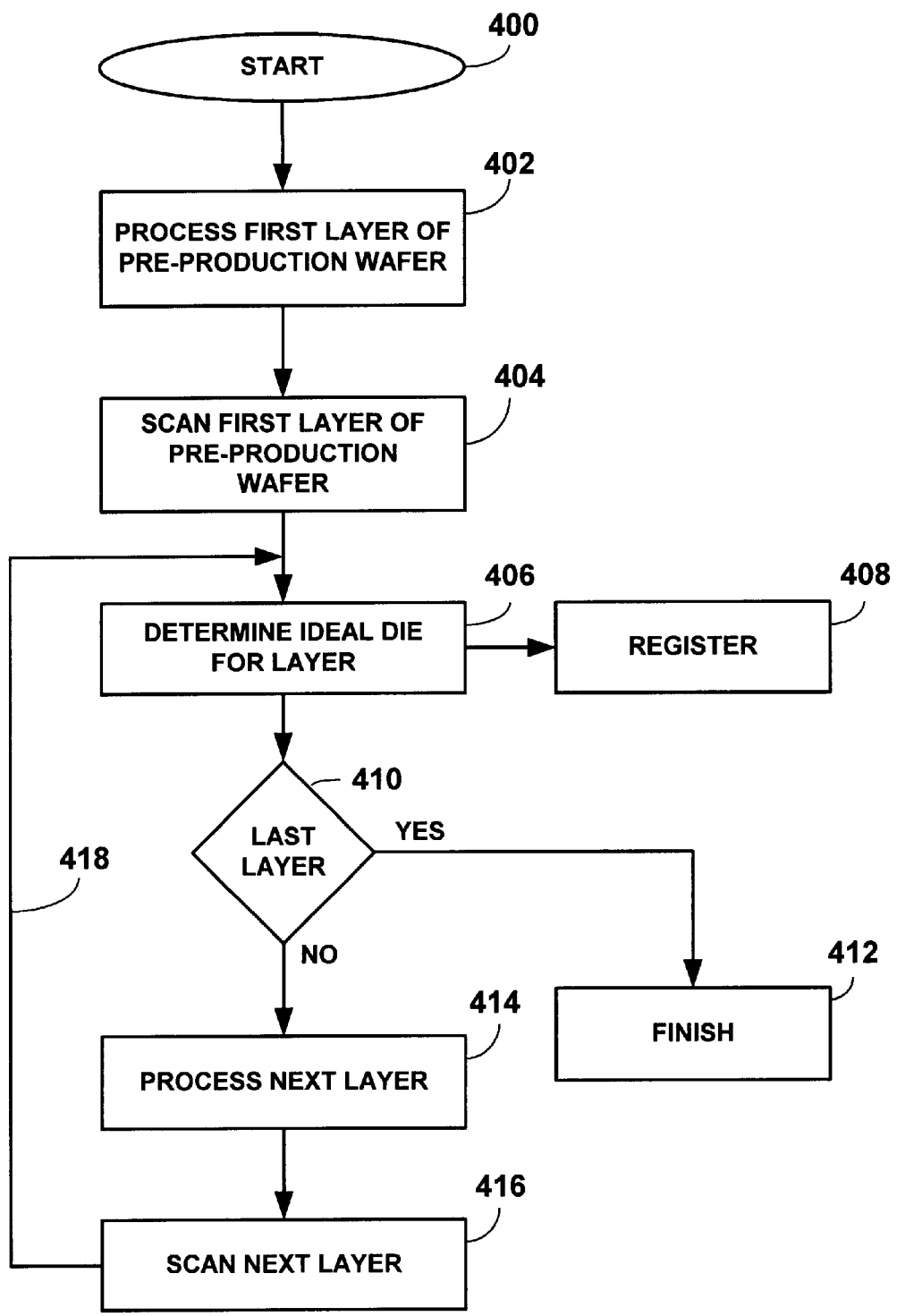
FIG. 4 is a flow diagram of the methodology to determine ideal die in accordance with present invention as diagrammed in FIG. 3.

FIG. 4 is a flow diagram of the methodology for scanning a pre-production semiconductor wafer to determined ideal die data in accordance with the present invention and which is diagrammed in FIG. 3. A pre-production wafer is started through a manufacturing process as indicated at 400. A first layer is processed 402, scanned 404 and data for an ideal for the first layer is determined 406 and stored in register 408. It is determined at 410 if the layer just scanned is the last layer, if yes, the process is finished 412. If the layer just scanned is not the last layer, the next layer of the wafer is processed 414 and scanned 416. The process is repeated as indicated at 418.

Figure 5:
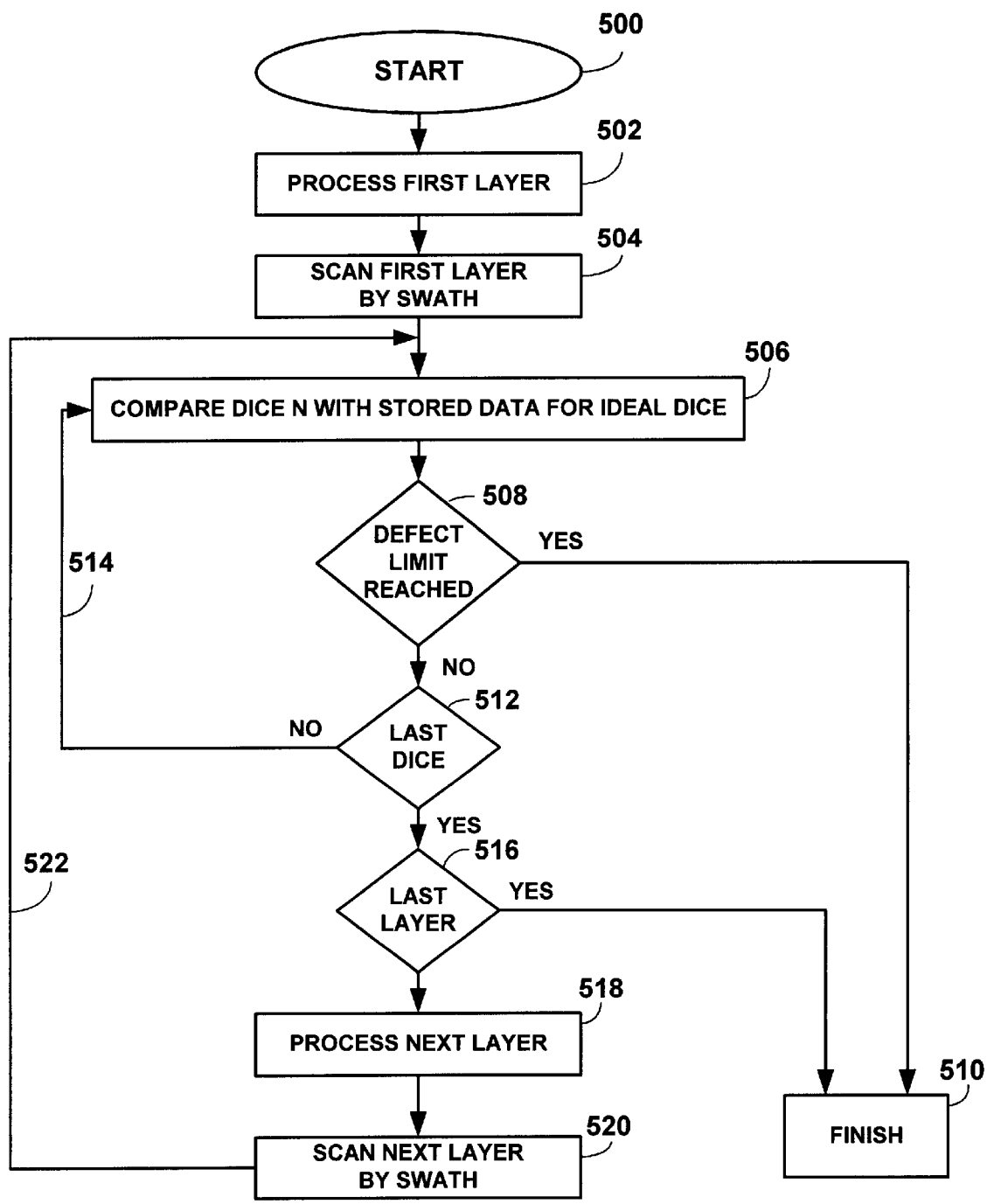
FIG. 5 is a flow diagram of the methodology to compare die in a wafer with the ideal die determined as shown in FIG. 4.

FIG. 5 is a flow diagram of the methodology of the present invention as diagrammed in FIG. 3. A production wafer is started in a manufacturing process as indicated at 500. The first layer process is completed 502, the first layer is optically scanned 504 and the optically scanned data for each dice N is compared to stored data for an ideal dice for the layer being scanned 506. It is determined at 508 whether a defect limit has been reached, if yes, the process is finished 510. If no, it is determined at 512 whether the last dice has been scanned, if no, the process continues as indicated at 514. If the last dice has been scanned, it is determined at 516 whether the last layer has been scanned. If the last layer has been scanned, the process is finished as indicated at 510. If the last layer has not been scanned, the next layer is processed 518, scanned 520 and the comparison process repeats, as indicated at 522.

The benefits of the present invention are that:
1. Complete wafer level information can be obtained without impacting manufacturing throughput.
2. The method of the present invention allows for monitoring uniformly distributed process problems.
3. The method of the present invention enables monitoring process variations over time.
4. The method of the present invention allows monitoring process integrity on a macro as well as on a micro level.
5. The method of the present invention allows monitoring of process drift in individual equipment, evolution as will as abrupt change.

In summary, the results and advantages of the methodology of the present invention can now be more fully realized. The present invention provides for ideal data, optical or otherwise, for a dice to be stored which can be compared to data from each dice on a production wafer. The method of the present invention is effective if the entire wafer is affected uniformly with induced defects, such as very wide or narrow CDs, over or under etch conditions (pitting, color variation, etc.) and unstripped resist.

The foregoing description of the embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of detecting defects on dice in a semiconductor wafer, the method comprising:

processing a first layer of a semiconductor wafer wherein the layer of a semiconductor wafer is formed into dice; and scanning the dice in the first layer of the semiconductor wafer and comparing data from each dice in the first layer of the semiconductor wafer with data from an ideal dice wherein the data from the ideal dice is obtained from a pre-production wafer.

2. The method of claim 1 further comprising processing a next layer of a semiconductor wafer and scanning the dice in the next layer of the semiconductor wafer and comparing data from each dice in the next layer of the semiconductor wafer with data from the ideal dice.

3. The method of claim 2 wherein the data from the ideal dice is obtained from a pre-production wafer wherein individual layers in the pre-production wafer are scanned and an ideal dice is determined for each layer and data from the ideal dice for each layer is stored in a register.

4. The method of claim 2 wherein comparing data from each dice in a layer in a semiconductor wafer is accomplished in a comparator with inputs from a scanner and from the register.

5. The method of claim 4 wherein scanning the dice in the first layer and the next layer and the pre-production wafer is accomplished in an optical scanner.

* * * * *